(12) United States Patent
Schwarz et al.

(10) Patent No.: US 7,433,055 B2
(45) Date of Patent: *Oct. 7, 2008

(54) DEVICE FOR THE EXAMINATION OF OPTICAL PROPERTIES OF SURFACES

(75) Inventors: Peter Schwarz, Königsdorf (DE); Uwe Sperling, Geretsried (DE)

(73) Assignee: BYK Gardner GmbH, Geretsried (DE)

( * ) Notice: Subject to any disclaimer, the term of this patent is extended or adjusted under 35 U.S.C. 154(b) by 333 days.

This patent is subject to a terminal disclaimer.

(21) Appl. No.: 11/175,903

(22) Filed: Jul. 6, 2005

(65) Prior Publication Data
US 2006/0092417 A1 May 4, 2006

(30) Foreign Application Priority Data
Jul. 15, 2004 (DE) .................. 10 2004 034 160

(51) Int. Cl.
*G01B 11/30* (2006.01)
(52) U.S. Cl. ................. 356/600; 356/446
(58) Field of Classification Search ......... 356/445–448, 356/600, 236; 250/228
See application file for complete search history.

(56) References Cited

U.S. PATENT DOCUMENTS

| | | | | |
|---|---|---|---|---|
| 4,479,718 A | * | 10/1984 | Alman | 356/405 |
| 4,917,495 A | * | 4/1990 | Steenhoek | 356/328 |
| 5,583,642 A | * | 12/1996 | Nakazono | 356/405 |
| 6,018,396 A | * | 1/2000 | Rapaport et al. | 356/446 |
| 6,975,404 B2 | * | 12/2005 | Schwarz | 356/446 |
| 7,177,032 B2 | * | 2/2007 | Lex | 356/600 |
| 7,276,719 B2 | * | 10/2007 | Schwarz | 250/559.36 |
| 2003/0151746 A1 | * | 8/2003 | Sperling et al. | 356/446 |
| 2005/0030542 A1 | * | 2/2005 | Schwarz | 356/445 |
| 2005/0094136 A1 | * | 5/2005 | Xu et al. | 356/237.3 |
| 2006/0033058 A1 | * | 2/2006 | Schwarz | 250/559.39 |
| 2006/0033922 A1 | * | 2/2006 | Sperling et al. | 356/446 |
| 2006/0274317 A1 | * | 12/2006 | Schwarz et al. | 356/446 |
| 2008/0013074 A1 | * | 1/2008 | Schwarz et al. | 356/73 |

* cited by examiner

*Primary Examiner*—Hoa Q Pham
(74) *Attorney, Agent, or Firm*—Greer, Burns & Crain, Ltd.

(57) ABSTRACT

A device for examining the optical properties of surfaces includes at least one first radiation device which emits radiation to a surface to be examined at a first predetermined spatial angle; at least one first detector device for capturing the radiation emitted to and reflected back from the surface, wherein the first detector device, allowing a local resolution of detected radiation, is positioned at least at a second predetermined spatial angle relative to the surface; and at least one further radiation device or second detector device emitting radiation to the surface to be examined at a third predetermined spatial angle or detecting radiation emitted to and reflected back from the surface.

28 Claims, 4 Drawing Sheets

DEVICE FOR THE EXAMINATION OF OPTICAL PROPERTIES OF SURFACES

BACKGROUND

The present invention relates to a device for examining the optical properties of surfaces. The device will be described below with reference to examining vehicle bodies. However, reference is made to the fact that other kinds of surfaces may also be examined with the device of the invention.

Such devices for examining the optical properties of surfaces are known from the prior art. Generally, these use a light source which emits light to the surface to be examined and a detector that detects and evaluates the light reflected or diffused off said surface. Such evaluation allows a determination of the optical properties of surfaces such as color or gloss. Such determination or characterization is required since motor-vehicle bodies or their paintwork make different impressions on the human eye depending on the incident light, thus requiring a neutral characterization.

Lately finishes have been gaining popularity which in particular comprise pigments or so-called flakes. These pigments or flakes are for instance metal particles statistically distributed in the layer of finish or its surface. More precisely, metal pigments may consist of very thin metal flakes acting as miniature reflectors. Standardizing this type of finishes or measuring the properties of their surfaces creates problems since, depending on the incidence angle of the light, said pigments exhibit different characteristics and for example the slightest variation of the viewing angle may already result in a different color or a different brightness. Among other things manufacturers also use finishes having interference pigments which, in particular in viewing large surface areas, result in color blending at more or less precisely specified color changing angles (flop) which may lead to largely different color perceptions which in turn leads to varying overall impressions of the brightness or the color of the finished surfaces.

These effects and different perceptions of surfaces caused for example by different densities, distribution and compositions of finish additives such as flakes or ornamental pigments cannot be detected with prior art devices since those detectors only supply information on the composite intensity of the incident light from various positions on the measuring surface i.e. they integrate intensity without local resolution.

SUMMARY OF THE INVENTION

It is therefore the object of the present invention to include in the examination of the properties of surfaces a resolution of such changes as caused specifically by shifting views of finished surfaces for example at slightly different spatial angles.

The device of the present invention for examining the optical properties of surfaces comprises at least one first radiation means which emits radiation to the surface to be examined at a first predetermined spatial subangle. In addition at least one first detector means is provided for capturing the radiation emitted to and reflected back from at least a portion of the surface wherein said detector means allows local resolution of the detected radiation and is positioned at a second predetermined spatial subangle relative to the surface.

A spatial angle is understood to mean within the scope of the present invention, as distinguished from the mathematical concept of a spatial angle, a tuple of spatial subangles. Herein the first component of the spatial angle, i.e. the first spatial subangle $\alpha$, refers to the projection angle onto the x/z plane relative to the positive z axis of a direction in space defined by a half straight line beginning in the point of origin in a Cartesian coordinate system.

Furthermore, the second component of the spatial angle, i.e. the second spatial subangle $\beta$, refers to the projection angle of said half straight line to the y/z plane relative to the positive z axis. Herein the coordinate system is oriented such that the measuring surface or at least portions of the measuring surface lie on the x/y plane.

The spatial angle is thus suitable for clearly characterizing the orientation of the radiation or detector means relative to the surface to be examined. The geometrical orientation of the spatial angles will be illustrated again in the description of the figures. A spatial angle of (0°, 0°) is understood to mean a spatial angle where the radiation or detector means is positioned above the surface to be examined such that the radiation emitting for example from the radiation means is incident on the surface to be examined substantially perpendicularly.

Further at least one further radiation means or detector means is provided which emits radiation to the surface to be examined or detects at least a portion of the radiation emitted to and reflected back from the surface.

Preferably said further radiation means emits directional radiation to the surface to be examined. In another preferred embodiment said further radiation means emits diffused radiation.

Radiation means is understood to mean a radiation source or a light source, in particular but not exclusively in the shape of light-emitting and/or laser diodes, light bulbs, halogen light bulbs and the like. A configuration of a number of light sources such as a number of light-emitting diodes having different emission spectra is also understood to mean a radiation means.

A detector means is understood to be any means capable of detecting at least one parameter of incident light and emitting a signal corresponding to said parameter. Detector means is intended to include both photo sensors, photo cells, photo elements and photo detectors and also for example cameras, CCD chips and the like.

Preferably the first detector means comprises a preferably plane image-capturing component which allows a local resolution of detected radiation. Said plane component may for example be a CCD chip capable of examining incident radiation with local resolution and preferably in addition also color resolution. Said examination with local resolution allows examining the effects generated by the individual pigments or flakes.

In contrast to this, a plane detector without local resolution would, only by integrating the intensity of radiation incident on each individual point on the detector surface across the surface, determine the composite intensity of the incident radiation and thus would not provide information on a local origin.

In order to achieve that examination also takes into account effects caused by differing incident light or incident light at different spatial angles it is also possible on the one hand to provide a number of light sources radiating onto the surface at different spatial angles. On the other hand it is also possible to provide instead of a number of radiation sources, a number of detectors allowing detection at different spatial angles.

Furthermore it would also be possible to provide a combination, i.e. a number of radiation means and a number of detector means.

In another preferred embodiment said radiation means and said detector means are positioned in one common housing that is substantially opaque to radiation and comprises an opening through which radiation is guided onto the surface to be examined. In this way one can assure that substantially only such light enters the individual detectors as is reflected back from the surface to be examined.

In another preferred embodiment at least two radiation means emit radiation on said surface concurrently, at least intermittently. Preferably it is therefore possible that only said first or only said second or both radiation means concurrently emit radiation on said surface. If more than two radiation means are provided in another embodiment it is conceivable to activate only individual ones or random combinations—or all—of said number of radiation means.

In this way different results can be obtained for the surface to be examined such as information on surface behavior with radiation at one predetermined angle only, or further data for concurrent radiation at a number of angles. In this way one can for example achieve an approximation to diffused daylight or a characterization of gloss.

In another preferred embodiment said second detector means is selected from a group of detector means comprising photo cells, photo elements, photo diodes and the like. As stated above, these elements do not permit local resolution of the examined radiation but only an examination of the radiation intensity and the spectral characteristics.

The preferred radiation means for resolving the spectral characteristics is a plurality of LCDs which substantially cover the entire spectrum of visible light. In this way a spectral resolution of the receiver means or detector means is achieved. However, it is also possible to use frequency-selective elements such as optical gratings in the ray path after the surface to be examined.

In another preferred embodiment said first detector means which allows local resolution of examined radiation also comprises means for determining the total intensity of incident radiation. This can be done in particular but not exclusively through integration of the incidence intensities on the individual photo cells of a CCD chip.

In another preferred embodiment the first detector means is positioned at a first spatial subangle of substantially 0° above the surface. Preferably said first detector means is also positioned at a second spatial subangle of 0° above the surface, meaning—as described above—that preferably it detects radiation emitting substantially perpendicularly from the surface to be examined.

In another preferred embodiment at least one radiation means is positioned at a first spatial subangle relative to the surface selected from a group of angles including −45°, −15° and +75°. Preferably said second spatial subangle is 0°.

The specified angles are to be understood as approximate values insofar as an angle for example of 45° is understood to include angles within a tolerance range of ±5°, i.e. angles between 40° and 50°.

In another preferred embodiment a plurality of radiation means is provided at predetermined angles. First spatial subangles of −15°, −45°, or +45° and +75° are preferably used. Otherwise it is also possible to use one radiation source and to position the respective detector means at predetermined first spatial subangles such as in particular but not exclusively −75°, −65°, −45°, −15° or 20°. Any other desired detection or incidence angles may of course be chosen. However, the magnitudes indicated refer to standards some of which are gauged. Thus far, however, no large first spatial subangles have been used in the prior art, i.e. spatial angles comparatively close to ($\alpha$=−90°) or ($\alpha$=+90°). Using such spatial angles allows a better characterization of pigments or their distribution on the surface. Preferably at least one detector means is positioned at such a first spatial subangle whose amount is larger than (70°, $\beta$) and preferably larger than (75°, $\beta$).

Preferably said first and said second spatial angles are chosen such that a large difference relative to said first spatial subangle will result, preferably a difference of more than 100°.

In another preferred embodiment at least one detector means is positioned at a first spatial subangle whose amount is small, preferably an angle whose amount is smaller than (30°, $\beta$) and particularly preferred smaller or equal (60°, $\beta$). Using such small spatial angles allows a better characterization of pigments having a substantial color shift.

Preferably said first and said second spatial angle are chosen such that a low difference relative to said first spatial subangle will result, preferably a difference of less than 50°.

In another preferred embodiment at least one radiation means emits non-directional or diffused radiation.

Directional radiation is understood to mean such radiation where the light is incident on the surface to be examined in a substantially predetermined direction or at a predetermined spatial angle. In another preferred embodiment at least one radiation means emits directional radiation (i.e. beams having a defined or sometimes a standardized aperture, whose rays are substantially parallel).

Non-directional radiation is understood to mean radiation incident on the surface to be examined at different spatial angles, for example after multiple reflection at the housing surface. This can be achieved in particular but not exclusively by using diffuser or frosted-glass plates.

In another preferred embodiment a number of radiation means are substantially positioned on an arc of a circle. In another preferred embodiment it is also conceivable that a number of detector means are substantially positioned on an arc of a circle or a number of radiation and detector means are substantially positioned on an arc of a circle. In this way it is achieved that the respective radiation means and/or detector means are substantially positioned at the same second spatial subangle or in one plane.

In a preferred embodiment said second spatial subangle at which the respective radiation and detector means are positioned is substantially 0°.

In another preferred embodiment at least one spatial subangle at which the first detector means is positioned is variable. This is preferably the first spatial subangle. A preferred embodiment provides that the first spatial subangle at which the first detector means is positioned relative to the surface to be examined, is variable between −90° and 90°.

In another preferred embodiment the first spatial subangle at which at least one radiation means is positioned, is variable. This means that the radiation means concerned can emit radiation to the surface from different directions. This variable spatial angle allows to achieve that in one measuring method for example light radiates initially at a predetermined spatial angle, then the first spatial subangle at which the radiation means is positioned is changed, and then radiation is emitted to the surface to be examined at the changed spatial angle.

Otherwise it is also possible, given a fixed first spatial subangle in the radiation means, to first position the detector means at a first spatial subangle and subsequently at a different spatial angle so as to obtain corresponding measuring results. Combinations are also conceivable, i.e. variable spatial angles in the radiation means and the detector means, such as a spatial angle of the detector means variable between (0, $\beta$) and (+90°, $\beta$) and the first spatial subangle of the radiation means variable from (0°, β) to (−90°, β). Preferably the second spatial subangle in the above embodiment is substantially 0°.

Another preferred embodiment provides means which allow that both a first detector means and a second detector means can detect radiation at the same predetermined spatial angle. These means may for example be beam splitters which cause a specified portion of the radiation to reach the first detector means and another portion, the second detector means. It is preferred that said first detector means allows a locally differentiating analysis of the radiation and the second detector means a locally integral intensity examination.

Other means are also conceivable such as partly silvered reflectors, polarizers and the like.

Another preferred embodiment provides a plurality of radiation means having predetermined, substantially regular, angular distances relative to one another. Said plurality is preferably positioned at the same second spatial subangles but at different first spatial subangles. In this case the angular distance will result from the difference of said first spatial subangle of a radiation means to that of an adjacent radiation means.

It is furthermore possible that the second spatial subangle is also variable, for example it is possible to jointly displace the plurality of radiation means with reference to the second spatial subangle. In another preferred embodiment a plurality of radiation means is positioned both at different first spatial subangles and different second spatial subangles.

It is likewise conceivable that a plurality of detector means are positioned at different first and second spatial subangles, and both a plurality of radiation means and a plurality of detector means which differ from one another in respect of their first and second spatial subangles.

The present invention further relates to a method for examining the optical properties of surfaces.

One process step provides a first radiation emitted to a surface to be examined at a first predetermined spatial subangle. Another process step provides that the radiation reflected back from the surface to be examined is detected by means of a first detector means at a second predetermined spatial angle wherein said detector means allows local resolution of the detected radiation.

Another process step provides that the radiation reflected back from the surface to be examined is detected by means of a second detector means at a third predetermined spatial angle.

Another method according to the invention provides a first process step wherein a first radiation is directed at a surface to be examined at a first predetermined spatial subangle.

Another process step provides that a second radiation is directed at the surface to be examined at a third predetermined spatial angle and another process step provides that the radiation reflected back from the surface to be examined is detected by means of a first detector means at a second predetermined spatial angle wherein said detector means allows local resolution of the detected radiation.

Preferably the first radiation and the second radiation are emitted concurrently, at least intermittently.

In another embodiment the first radiation and the second radiation are emitted time-shifted, at least intermittently. Preferably it is possible while measuring to emit radiation to the surface to be examined both concurrently and time-shifted since the two procedures serve to obtain different, relevant data on the optical properties of the surface to be examined.

BRIEF DESCRIPTION OF THE DRAWINGS

Further advantages and embodiments of the device of the present invention can be taken from the accompanying drawing. These show in.

DESCRIPTION OF THE PREFERRED EMBODIMENT

Figure 1:
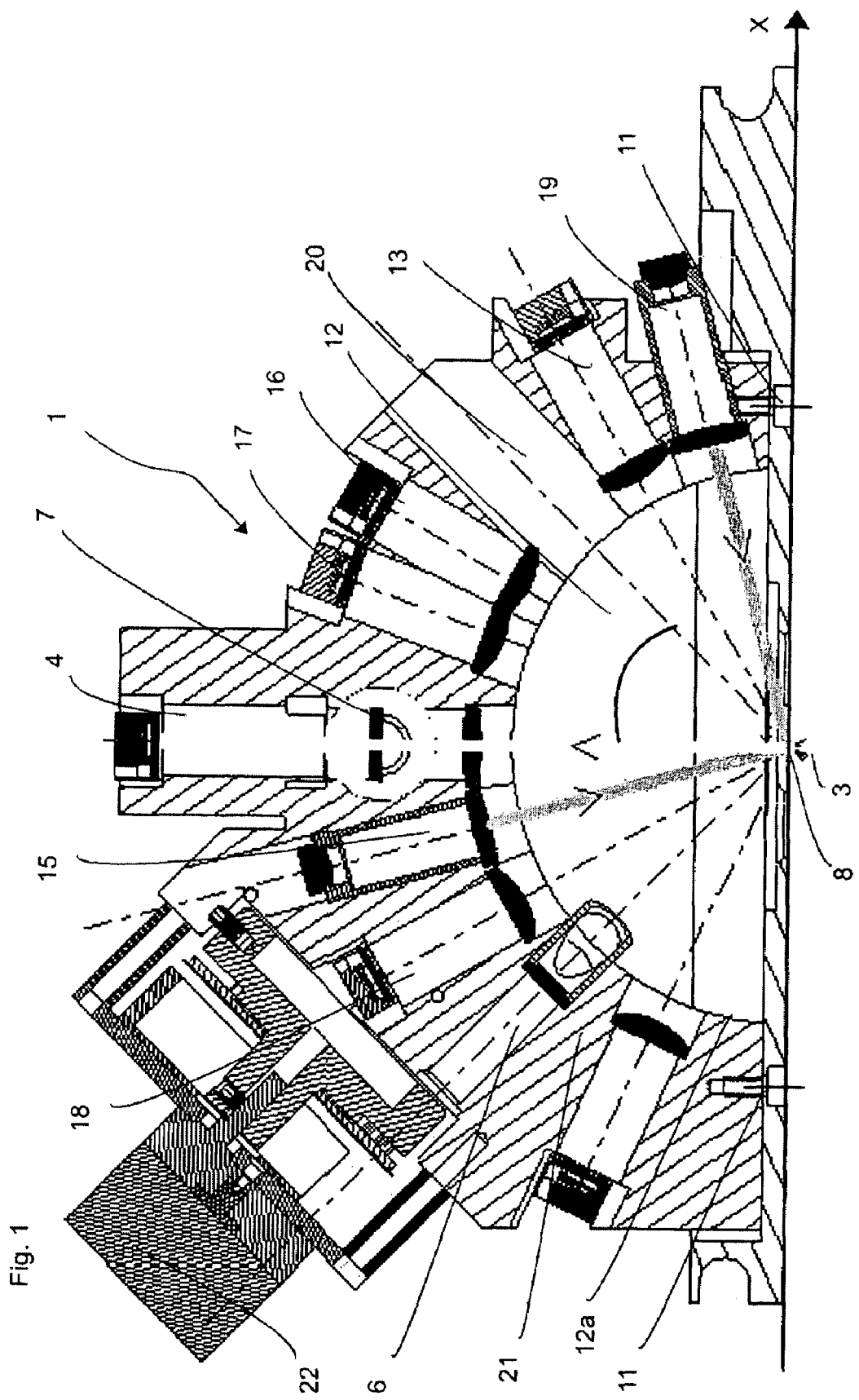
FIG. 1 is an embodiment of the present device for examining surfaces.

FIG. 1 shows an embodiment of a device 1 of the invention for examining optical surfaces. It comprises a housing 21 comprising a hollow space 12 in its interior. This hollow space is configured as a semicircle or, in three-dimensional view, as a hemisphere or a hemispherical segment. However, it is also conceivable to provide other structures for said hollow space. Preferably the inner surface of the hollow space absorbs substantially all radiation so as to avoid incorrect measuring results of directional light due to multiple reflections between the inner surface of the hollow space and the measuring surface. Other preferred embodiments provide a hollow space whose inner surface is configured of a substantially absorbing layer. In this way it can be achieved that non-collimated light is generated under predetermined measuring conditions such that the surface properties under diffused light conditions can be characterized.

The bottom surface of the housing comprises an opening 8 beneath which the surface 3 to be examined is positioned. Reference numeral 15 indicates a first radiation means and reference numeral 19, a second radiation means. Said radiation means 15, 19 emit light to the surface 3 to be examined at a predetermined spatial angle. Preferably said radiation is directional.

The first spatial subangles at which said radiation means 15 and 19 are positioned, are $\alpha=-15°$ or $\alpha=+75°$. A spatial subangle $\alpha=0°$ is understood to mean the angle at which light is directed from the surface 3 to be examined perpendicularly upwardly in FIG. 1.

In this case the angle β indicating the tilt of the configuration around the axis x is also 0°. The embodiment shown in FIG. 1 provides that all of the radiation directions are positioned on the surface 3 in a perpendicular plane running through the X tubes, i.e. the angle $\beta=0°$ for all of the radiation directions. Reference numeral 7 indicates a camera and reference numeral 4, a photo sensor. These two are positioned at an angle $\alpha=\beta=0°$, i.e. they detect the light emitting from the surface to be examined perpendicularly upwardly. The arrangement of camera and detector ensures that both measuring means detect or characterize the same light.

It is also conceivable to provide, instead of two radiation means 15 and 19, only one radiation means whose spatial angles may be freely selected. The camera 7 and the photo sensor 4 may be positioned at spatial angles deviating from (0°; 0°) possibly also at different angles.

The reference numerals 13, 14, 16, 17, and 18 indicate further photo detectors. In this specified embodiment the photo detectors are positioned at the spatial subangles α=−60° (photo detector 14), α=−30° (photo detector 18), α=20° (photo detector 17), α=30° (photo detector 16) and α=60° (photo detector 13). Another photo detector or another radiation means may be provided in the opening 20.

Alternatively it is conceivable to provide, in lieu of the detectors, more radiation means or to concurrently provide radiation means and detectors at the same or adjacent locations. This may for example be realized by means of beam splitters wherein for example dichroic reflectors and the like may be used.

For example a combined radiation and detector means can be configured such that a dichroic reflector positioned at 45° relative to a geometrical connecting line between the radiation means and the incidence point of the radiation on the surface, allows incidence of light emitting from a radiation means while in respect of reflecting back light reflected back from the surface to be examined it is substantially light-transmitting, substantially allowing it to pass through to a detector means.

Reference numerals 11 refer to an adjusting device which preferably serves to adjust the position of the device for examining surfaces relative to the surface to be examined. The housing section 22 may receive for example displays for the user, the control means of the individual detector means and radiation means, control means, motors and the like.

Figure 2:
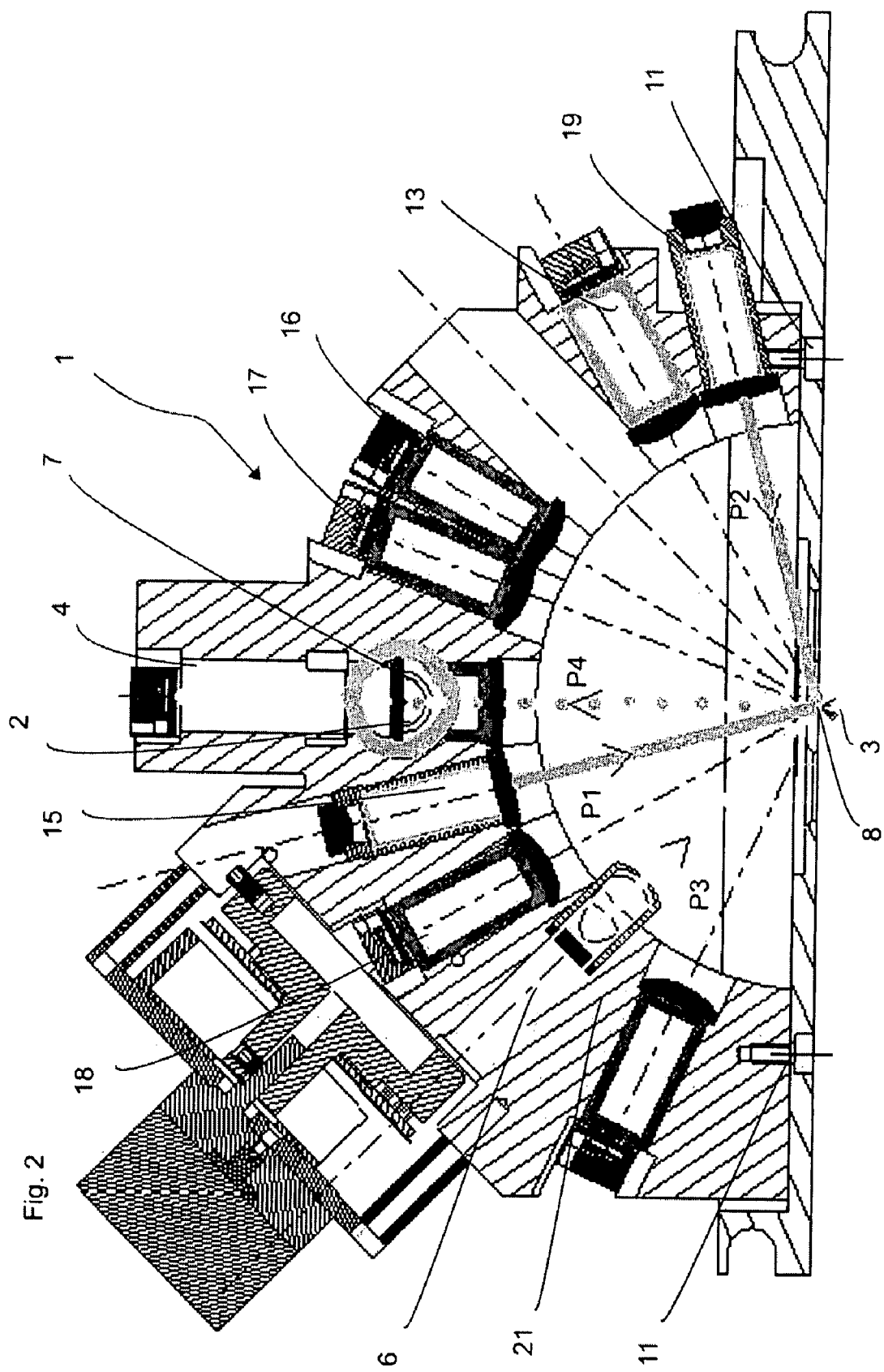
FIG. 2 is the embodiment of the device of FIG. 1, using another measuring method.

With reference to FIG. 2 the measuring method applied with the device of the invention will now be described. The arrows P1 and P2 indicate the light emitting from the radiation sources 15 and 19 incident on the surface 3. It radiates along the arrow P4 (illustrated as a dotted line) in the direction of the camera 7. The camera configuration 7 comprises a beam splitter system illustrated in FIGS. 4 to 7. Said beam splitter causes that the ray running along the arrow P4 is split, which ray is combined of a component originally emitting from the radiation means 6 along the arrow P3, and the above-mentioned rays originating from the radiation means 15 and 19.

Since the camera allows local resolution of the illustrated image, a local resolution of the surface to be examined can thus be displayed. In this way the individual pigments or flakes can be rendered visible.

The preferred use of a color camera allows color resolution.

Instead of the system employed herein which comprises both a camera 7 and a photo detector 4 it is also conceivable to capture the measurement only with a camera and to determine the integral intensity, in particular but not exclusively computer-aided from the image incident in the camera.

In this way it is possible to examine the details of the surface texture, i.e. the precise geometrical position of the pigments, on or in the individual layers of paint and thus to assess the effects resulting among other things from the density, distribution and type of the ornamental pigments used.

The light emitting from the radiation means 6 is also projected on the surface 3 where it is captured at different spatial angles. As mentioned above, the ray reflected back at (0°; 0°) is captured by the detector means 4. The illustrated embodiment further provides capturing by means of the detector means 13, 14, 16, 17 and 18 at the other spatial angles indicated above.

As mentioned above, the materials to be examined such as the finishes exhibit different optical properties depending on the direction from which they are illuminated. The individual detectors 13 to 18 will therefore generate different spectral results since they simulate different observation angles for example of a human observer.

Another embodiment provides use of a plurality of radiation means positioned at different spatial angles which also simulate different observation angles for example by means of a stationary detector. As mentioned above, the radiation means 19 is positioned at a first spatial subangle of 75°, i.e. the light emitting from said radiation means is projected onto the surface 3 to be examined at a comparatively steep angle. This arrangement of the radiation means 19 primarily serves to examine curved, in particular concave, surfaces.

Figure 5C:
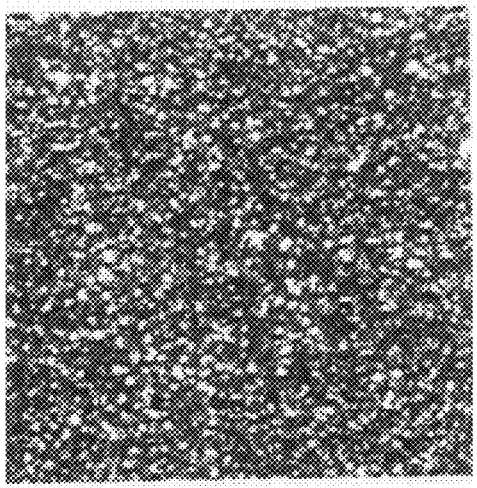
FIG. 5*c* is an illustration of the measuring result obtained with the embodiment of the device of FIG. 1.
Figure 5B:
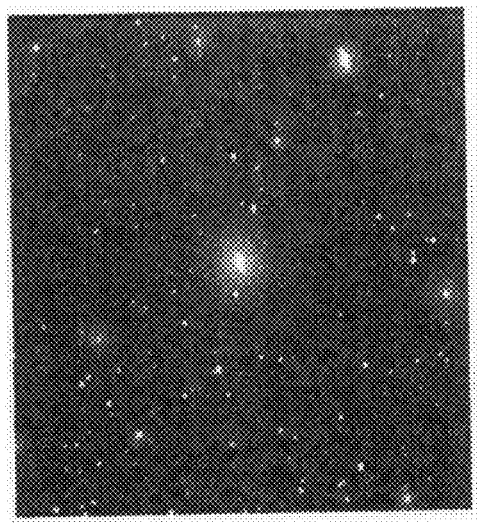
FIG. 5*b* is an illustration of the measuring result obtained with the embodiment of the device of FIG. 1.

This application is suitable for detecting pigments having high radiation intensity relative to the environment, as shown in FIG. 5b.

As mentioned above, the individual radiation means can be operated independently of one another. This means that it is possible to emit radiation on the surface only by one of the two radiation means 15 or 19 or concurrently by both. Or, the two variants may be combined to carry out a complete measuring cycle.

For examining gloss, this embodiment emits radiation on the surface concurrently with the two radiation means 15 and 19, and the camera 7 captures the image.

For examining graininess, the radiation means 15 in the illustrated embodiment is set to −15° for radiating, and detecting takes place at 0°.

In addition to the illustrated radiation means, another radiation means emitting non-directional radiation may be used. In this way one can for example simulate illumination of the surface 3 on overcast days. As specified above, non-directional radiation can be generated in particular but not exclusively through diffuser disks or individual radiation sources distributed across the space.

It is also conceivable to use directional and non-directional radiation jointly, for example consecutively or substantially concurrently.

Figure 3:
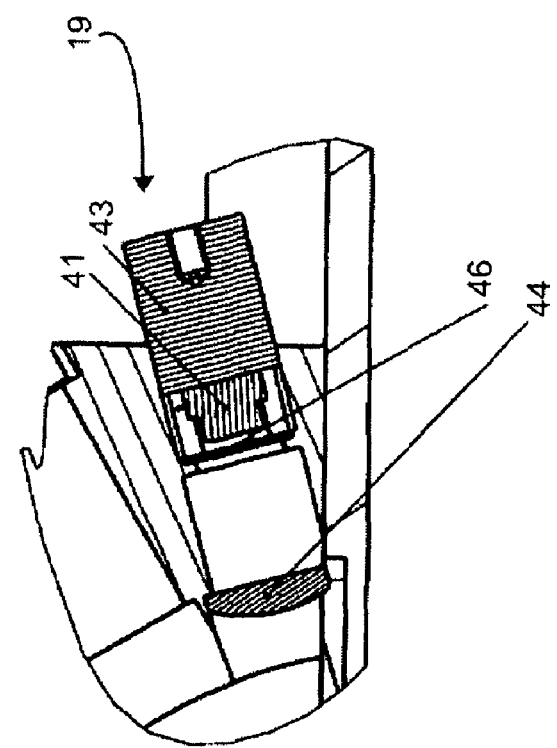
FIG. 3 is a detailed view of the embodiment of the device of FIG. 1.

FIG. 3 shows a detailed view of the radiation means 19. It comprises a high performance LED 41 placed in a housing 43. Furthermore an aperture 46 is provided and a lens 44 to direct collimated light at the surface. In addition to one light-emitting diode, a number of light-emitting diodes may be provided having different emission spectra in particular in visible range. Also, the individual radiation means may comprise light-emitting diodes having different emission spectra. Further, radiation means may be provided emitting substantially white light or light approximated to white light.

Figure 4:
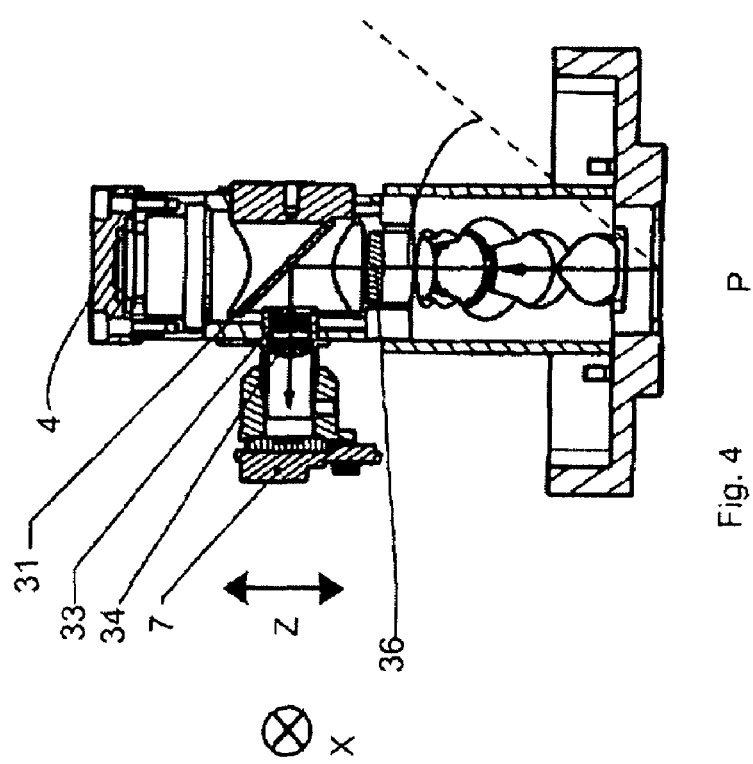
FIG. 4 is a sectional view of the device of FIG. 1.

FIG. 4 shows a lateral cross-sectional view of the device of the invention in FIG. 1. As discussed above, all of the radiation means and detector means herein are positioned at a spatial subangle β=0°. The dashed line indicates the spatial subangle β where the device would be positioned at 45°. A preferred embodiment provides that the device can be tilted about the point P on the axis x shown in FIG. 1. In this way it is possible to radiate and to detect light substantially at any desired spatial subangle β.

As mentioned, the device of the invention comprises a beam splitter system 2 for directing at the camera the light projected onto the surface in FIG. 2 along the arrows P1 and P3 and reflected back along the arrow P4. It is deflected through a beam splitter 31 substantially by 90° and guided through a filter and a lens to the camera 7 or the photosensitive surface. Another portion (not shown) of the light is guided on to the detector means 4.

Another preferred embodiment provides that the position of the camera 7 or the photosensitive surface is displaced relative to the beam S, preferably in the Z and X directions which run vertically in the drawing plane or perpendicularly in the drawing plane, respectively. It is further possible to provide at the bottom surface of the housing 39 adjusting devices (not shown) to position the device precisely, for example perpendicularly, relative to the surface to be examined.

Figure 5A:
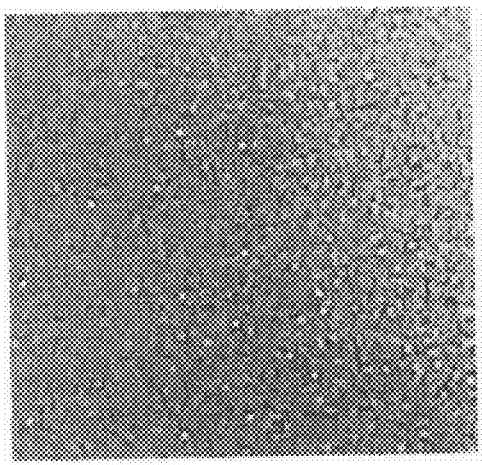
FIG. 5*a* is an illustration of the measuring result obtained with the embodiment of the device FIG. 1.

The FIGS. 5a, 5b and 5c show examples of the surface effects which the device of the invention can capture. FIG. 5a illustrates a color shift because of a curved surface. Said color shift can for example be examined by means of a color picture camera. One can examine in detail which changes of the incidence and detection angle lead to which changes in color and brightness. Further embodiments provide to use, not a black-and-white camera but a color camera which provides additional information on the colors of the individual pigments. Use of a black-and-white camera and a plurality of radiation sources having different emission spectra will also provide information on the color of the pigments.

Figure 5D:
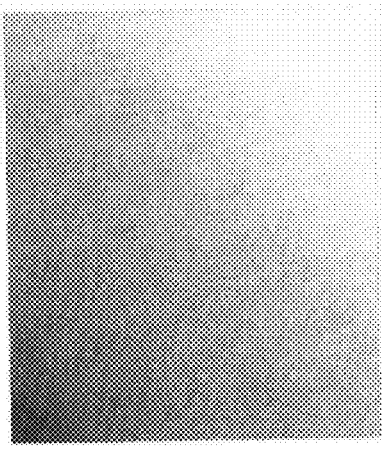
FIG. 5*d* is a representation to illustrate the measuring result.

It is also apparent that this capturing arrangement allows to capture light/dark contrasts resulting from different observation angles. While the image appears somewhat darker in the top left area, it is brighter in the lower right area. FIG. 5d does not show a camera-captured image of the surface but a schematic illustration of the brightness pattern illustrated in FIG. 5a. Depending on the observation angles, reflection differs largely between the individual pigments and in this way creates the light/dark transitions illustrated.

FIG. 5b is a camera-captured measurement of the surface wherein a corresponding spatial angle β (75°, β) of the radiation means causes individual pigments or flakes to reflect particularly intensely. Such capturing allows to examine the distribution of the individual pigments or also their sizes and reflective capabilities. For generating the captured measurement illustrated in FIG. 5b it is preferred to use an incidence or first spatial subangle α of a high value. Since the camera detects beneath 0°, the absolute majority of the light reflected off the surface does not enter the camera such that the effect of the flakes can be measured with a minimum of background illumination. The illustration of FIG. 5b shows individual pigments.

FIG. 5c illustrates the structure of the surface to be examined. In this way the graininess of the surface can be determined by radiating diffused light or at a suitable incidence angle.

It is also possible to obtain the image shown in FIG. 5c by varying the camera resolution. Another embodiment provides the use of digital filters for this purpose.

The invention claimed is:

1. A device for examining the optical properties of surfaces comprising:
   at least one first radiation means—emitting radiation at a first predetermined spatial angle to a surface to be examined;
   at least one first detector means for capturing the radiation emitted to and reflected back from the surface wherein said first detector means comprises an image-capturing component, allowing a local resolution of detected radiation, wherein said first detector means is positioned at a second predetermined spatial angle relative to said surface;
   at least one second radiation means which emits radiation to the surface to be examined, said at least one first and second radiation means being arranged at different spatial angles relative to the surface to be examined for emitting radiation onto the surface; and
   at least one second detector means which detects radiation emitted to and reflected back from the surface to be examined, wherein said second detector means is arranged at a third predetermined spatial angle and does not permit local resolution;
   wherein said first, second and third spatial angles are each defined by a tupel of a first spatial subangle and a second spatial subangle each indicating a projection angle relative to a surface perpendicular to the surface to be examined; and
   wherein said tupel of said second spatial angle is (0°, 0°), such that said second spatial angle is perpendicular above the surface to be examined.

2. The device according to claim 1, wherein said second radiation means emits diffused radiation.

3. The device according to claim 1 wherein said second radiation means emits directional radiation.

4. The device according to claim 1, wherein said first detector means comprises a plane image-capturing component which allows a local resolution of detected radiation.

5. The device according to claim 1, wherein said first detector means comprises a plane image-capturing component which allows a color resolution of detected radiation.

6. The device according to claim 1, wherein said first detector means is selected from a group of detector means including cameras and CCD chips.

7. The device according to claim 1 wherein said radiation means and said detector means are positioned in a common housing that is substantially opaque to radiation and comprises an opening through which radiation is guided onto the surface to be examined.

8. The device according to claim 1 wherein at least two said radiation means emit radiation on said surface concurrently, at least intermittently.

9. The device according to claim 1 wherein said second detector means is selected from a group of detector means including photo cells, photo elements and photo diodes.

10. The device according to claim 1 wherein one of said at least one first radiation means and said at least one second radiation means is positioned relative to the surface at said first spatial subangle selected from a group of angles including −45°, −15° and 75°.

11. The device according to claim 1 wherein one of said at least one first radiation means and said at least one second radiation means is positioned relative to the surface at said first spatial subangle whose amount is larger than 70°.

12. The device according to claim 1 wherein said at least one detector means is positioned relative to the surface at said second spatial subangle whose amount is larger than 70°.

13. The device according to claim 1 including at least two second detector means each positioned relative to the surface at said second spatial subangle selected from a group of angles including −75°, −15°, 25°, 45°, 75° and 110°.

14. The device according to claim 1 wherein said at least one radiation means emits directional radiation.

15. The device according to claim 1 wherein said at least one radiation means emits non-directional radiation.

16. The device according to claim 1 including a plurality of radiation means each substantially positioned on an arc of a circle.

17. The device according to claim 1 including a plurality of detector means each substantially positioned on an arc of a circle.

18. The device according to claim 1 wherein said radiation means and said detector means are substantially positioned at the same second spatial subangle.

19. The device according to claim 18 wherein said at least one second spatial subangle at which said first detector means is positioned, is variable.

20. The device according to claim 18 wherein said predetermined first spatial subangle at which at least one radiation means is positioned, is variable.

21. The device according to claim 18 wherein said predetermined second spatial subangle at which at least one detector means is positioned, is variable.

22. The device according to claim 1 wherein said both said radiation means and said detector means are substantially positioned on an arc of a circle.

23. The device according to claim 1 wherein said first detector means and said second detector means can detect radiation at the same predetermined spatial angle.

24. The device according to claim 1 wherein said plurality of radiation means are provided whose spatial angular distance relative to one another is predetermined and substantially constant.

25. A method for examining the properties of optical surfaces including the steps:
   directing a first radiation at a surface to be examined at a first predetermined spatial subangle;
   detecting the radiation reflected back from the surface to be examined by means of a first detector means at a second predetermined spatial angle, wherein said detector means allows a local resolution of detected radiation; and
   detecting the radiation reflected back from the surface to be examined by means of a second detector means at a third predetermined spatial angle, wherein said second detector means does not permit a local resolution;
   wherein said second and third spatial angles are each defined by a tupel of said first spatial subangle and a second spatial subangle each indicating a projection angle relative to a surface perpendicular to the surface to be examined; and
   wherein said tupel of said second spatial angle is (0°, 0°) such that the first detector means is arranged perpendicular above the surface to be examined.

26. A method for examining the properties of optical surfaces including the steps:
   directing a first diffused radiation at a surface to be examined at a first predetermined spatial subangle;
   directing a second directional radiation at a surface to be examined at a third predetermined spatial angle; and
   detecting the radiation reflected back from the surface to be examined by means of a first detector means at a second predetermined spatial angle, wherein said detector means allows a local resolution of detected radiation;
   wherein said second and third spatial angles are each defined by a tupel of a first spatial subangle and a second spatial subangle each indicating a projection angle relative to a surface perpendicular to the surface to be examined; and
   wherein said tupel of said second spatial angle is (0°, 0°) such that the first detector means is arranged perpendicular above the surface to be examined.

27. The method according to claim 25 further including directing said first radiation and said second radiation occurs concurrently, at least intermittently.

28. The method according to claim 25 further including directing said first radiation and said second radiation occurs time-shifted, at least intermittently.

* * * * *